(12) United States Patent
Sniffin et al.

(10) Patent No.: US 8,496,156 B2
(45) Date of Patent: Jul. 30, 2013

(54) CARTRIDGE FOR APPLYING VARYING AMOUNTS OF TISSUE COMPRESSION

(75) Inventors: Kevin Sniffin, Danbury, CT (US); Michael Soltz, Springfield, NJ (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/585,377

(22) Filed: Aug. 14, 2012

(65) Prior Publication Data

US 2012/0305628 A1    Dec. 6, 2012

Related U.S. Application Data

(63) Continuation of application No. 13/228,017, filed on Sep. 8, 2011, now Pat. No. 8,256,655, which is a continuation of application No. 12/422,501, filed on Apr. 13, 2009, now Pat. No. 8,028,884.

(60) Provisional application No. 61/046,883, filed on Apr. 22, 2008.

(51) Int. Cl.
*A61B 17/068* (2006.01)
(52) U.S. Cl.
USPC ............................................ 227/176.1; 227/19
(58) Field of Classification Search
USPC ...................... 227/176.1, 19, 175.1
See application file for complete search history.

(56) References Cited

U.S. PATENT DOCUMENTS

| | | | |
|---|---|---|---|
| 3,771,526 A | 11/1973 | Rudie | |
| 4,319,576 A | 3/1982 | Rothfuss | |
| 4,605,001 A | 8/1986 | Rothfuss et al. | |
| 4,606,343 A | 8/1986 | Conta et al. | |
| 4,608,981 A | 9/1986 | Rothfuss et al. | |
| 4,610,383 A | 9/1986 | Rothfuss et al. | |
| 4,741,336 A | 5/1988 | Failla et al. | |
| 4,767,044 A | 8/1988 | Green | |
| 4,809,695 A | 3/1989 | Gwathmey et al. | |
| 4,848,637 A | 7/1989 | Pruitt | |
| 4,930,503 A | 6/1990 | Pruitt | |
| 4,941,623 A | 7/1990 | Pruitt | |
| 4,978,049 A | 12/1990 | Green | |
| 5,027,834 A | 7/1991 | Pruitt | |
| 5,108,422 A | 4/1992 | Green et al. | |

(Continued)

FOREIGN PATENT DOCUMENTS

| | | |
|---|---|---|
| EP | 0878169 | 11/1998 |
| EP | 0640315 | 12/1998 |

(Continued)

OTHER PUBLICATIONS

European Search Report for EP 06016963.8-2318 date of completion is Feb. 28, 2007.

(Continued)

*Primary Examiner* — Brian D Nash

(57) ABSTRACT

A surgical stapling apparatus includes a staple cartridge and an anvil member. The staple cartridge includes a plurality of surgical fasteners disposed in rows of retention slots. The staple cartridge may have an annular or linear configuration of retention slots. The tissue contacting surface of the staple cartridge may be tapered or stepped. The anvil member has a tissue contacting surface that includes a number of pockets arranged for substantially aligning with the retention slots. In addition, the tissue contacting surface of the anvil member may complement the tissue contacting surface of the staple cartridge.

9 Claims, 6 Drawing Sheets

U.S. PATENT DOCUMENTS

| | | | |
|---|---|---|---|
| 5,180,092 A | 1/1993 | Crainich |
| 5,201,746 A | 4/1993 | Shichman |
| 5,219,353 A | 6/1993 | Garvey, III et al. |
| 5,240,163 A | 8/1993 | Stein et al. |
| 5,282,829 A | 2/1994 | Hermes |
| 5,342,396 A | 8/1994 | Cook |
| 5,350,400 A | 9/1994 | Esposito et al. |
| 5,452,836 A | 9/1995 | Huitema et al. |
| 5,452,837 A | 9/1995 | Williamson, IV et al. |
| 5,484,095 A | 1/1996 | Green et al. |
| 5,497,931 A | 3/1996 | Nakamura |
| 5,501,693 A | 3/1996 | Gravener |
| 5,509,920 A | 4/1996 | Phillips et al. |
| 5,571,116 A | 11/1996 | Bolanos |
| 5,571,285 A | 11/1996 | Chow et al. |
| 5,634,926 A | 6/1997 | Jobe |
| 5,667,526 A | 9/1997 | Levin |
| 5,667,527 A | 9/1997 | Cook |
| 5,676,674 A | 10/1997 | Bolanos et al. |
| 5,685,474 A | 11/1997 | Seeber |
| 5,692,668 A | 12/1997 | Schulze et al. |
| 5,697,542 A | 12/1997 | Knodel et al. |
| 5,709,680 A | 1/1998 | Yates et al. |
| 5,741,268 A | 4/1998 | Schulz |
| 5,810,822 A | 9/1998 | Mortier |
| 5,865,361 A | 2/1999 | Milliman et al. |
| 5,871,135 A | 2/1999 | Williamson, IV et al. |
| 5,915,616 A | 6/1999 | Viola et al. |
| 5,964,394 A | 10/1999 | Robertson |
| 6,083,242 A | 7/2000 | Cook |
| H1904 H | 10/2000 | Yates et al. |
| 6,202,914 B1 | 3/2001 | Geiste et al. |
| 6,269,997 B1 | 8/2001 | Balazs et al. |
| 6,325,810 B1 | 12/2001 | Hamilton et al. |
| 6,348,054 B1 | 2/2002 | Allen |
| 6,786,382 B1 | 9/2004 | Hoffman |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,988,649 B2 | 1/2006 | Shelton, IV et al. |
| 7,000,818 B2 | 2/2006 | Shelton, IV et al. |
| 7,000,819 B2 | 2/2006 | Swayze et al. |
| 7,044,352 B2 | 5/2006 | Shelton, IV et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,303,106 B2 | 12/2007 | Milliman et al. |
| 7,438,209 B1 * | 10/2008 | Hess et al. ................ 227/180.1 |
| 7,455,676 B2 | 11/2008 | Holsten et al. |
| 7,588,174 B2 | 9/2009 | Holsten et al. |
| 2003/0057251 A1 | 3/2003 | Hartwick |
| 2004/0004105 A1 | 1/2004 | Jankowski |
| 2004/0073222 A1 | 4/2004 | Koseki |
| 2004/0232195 A1 | 11/2004 | Shelton et al. |
| 2004/0232199 A1 | 11/2004 | Shelton et al. |
| 2004/0247415 A1 | 12/2004 | Mangone, Jr. |
| 2005/0006430 A1 | 1/2005 | Wales |
| 2005/0006431 A1 | 1/2005 | Shelton et al. |
| 2005/0006434 A1 | 1/2005 | Wales |
| 2005/0023324 A1 | 2/2005 | Doll et al. |
| 2005/0023325 A1 | 2/2005 | Gresham et al. |
| 2005/0070925 A1 | 3/2005 | Shelton, IV et al. |
| 2005/0070958 A1 | 3/2005 | Swayze et al. |
| 2005/0173490 A1 | 8/2005 | Shelton, IV |
| 2005/0178813 A1 | 8/2005 | Swayze et al. |
| 2005/0187576 A1 | 8/2005 | Whitman et al. |
| 2005/0263562 A1 | 12/2005 | Shelton, IV et al. |
| 2005/0267530 A1 | 12/2005 | Cummins |
| 2006/0000868 A1 | 1/2006 | Shelton, IV et al. |
| 2006/0015144 A1 | 1/2006 | Burbank et al. |
| 2006/0022014 A1 | 2/2006 | Shelton, IV et al. |
| 2006/0022015 A1 | 2/2006 | Shelton, IV et al. |
| 2006/0025809 A1 | 2/2006 | Shelton, IV |
| 2006/0025810 A1 | 2/2006 | Shelton, IV |
| 2006/0025811 A1 | 2/2006 | Shelton, IV |
| 2006/0025812 A1 | 2/2006 | Shelton, IV |
| 2006/0025813 A1 | 2/2006 | Shelton, IV et al. |
| 2006/0025816 A1 | 2/2006 | Shelton, IV |
| 2006/0025817 A1 | 2/2006 | Ortiz et al. |
| 2006/0039779 A1 | 2/2006 | Ring |
| 2006/0049230 A1 | 3/2006 | Shelton, IV et al. |
| 2006/0097026 A1 | 5/2006 | Shelton, IV |
| 2006/0124688 A1 | 6/2006 | Racenet et al. |
| 2006/0226196 A1 | 10/2006 | Hueil et al. |
| 2007/0010838 A1 | 1/2007 | Shelton, IV et al. |
| 2007/0131732 A1 | 6/2007 | Holsten et al. |
| 2007/0179408 A1 | 8/2007 | Soltz |
| 2008/0041918 A1 | 2/2008 | Holsten et al. |
| 2008/0082126 A1 * | 4/2008 | Murray et al. ................ 606/221 |
| 2008/0197167 A1 | 8/2008 | Viola et al. |
| 2008/0210738 A1 * | 9/2008 | Shelton et al. ............. 227/176.1 |

FOREIGN PATENT DOCUMENTS

| | | |
|---|---|---|
| EP | 1090592 | 4/2001 |
| EP | 1316290 | 6/2003 |
| EP | 1479346 | 11/2004 |
| FR | 2838952 | 10/2003 |
| SU | 405234 | 9/1975 |
| SU | 1333319 | 8/1987 |
| SU | 1442191 | 12/1988 |
| SU | 1459659 | 2/1989 |
| WO | WO 90/05489 | 5/1990 |
| WO | WO 97/34533 | 9/1997 |
| WO | WO 03/094743 | 11/2003 |
| WO | WO 03/094747 | 11/2003 |

OTHER PUBLICATIONS

European Search Report for EP 09251138.5-2310 date of completion is May 3, 2010.

* cited by examiner

CARTRIDGE FOR APPLYING VARYING AMOUNTS OF TISSUE COMPRESSION

CROSS REFERENCE TO RELATED APPLICATION

This application is a continuation of U.S. application Ser. No. 13/228,017 filed Sep. 8, 2011, now U.S. Pat. No. 8,256,655, which is a continuation of U.S. application Ser. No. 12/422,501 filed Apr. 13, 2009, now U.S. Pat. No. 8,028,884, which claims benefit of application No. 61/046,883 filed on Apr. 22, 2008, and the disclosures of each of the above-identified applications are hereby incorporated by reference in their entirety.

BACKGROUND

1. Technical Field

The present disclosure relates to surgical fastener apparatus and surgical fastener cartridges, and more particularly, to apparatus and cartridges for applying varying amounts of tissue compression.

2. Background of Related Art

Many varieties of surgical fastening apparatus are known in the art, some of which are specifically adapted for use in various surgical procedures including, but not limited to, end-to-end anastomosis, circular end-to-end anastomosis, open gastrointestinal anastomosis, endoscopic gastrointestinal anastomosis, and transverse anastomosis. Suitable examples of apparatus which may be used during the course these procedures can be seen in U.S. Pat. Nos. 5,915,616; 6,202,914; 5,865,361; and 5,964,394.

In general, a surgical fastening apparatus will include an anvil that is approximated relative to a fastener cartridge during use. The anvil includes depressions that are aligned with, and/or are in registration with slots defined in the cartridge, through which the fasteners will emerge, to effectuate formation. The fastener cartridge typically has one or more rows of fasteners disposed laterally or radially of a channel that is configured to accommodate a knife, or other such cutting element, such that tissue can be simultaneously cut and joined together. Depending upon the particular surgical fastening apparatus, the rows of fasteners may be arranged in a linear or non-linear, e.g. circular, semi-circular, or otherwise arcuate configuration.

Various types of surgical fasteners are well known in the art, including but not limited to unitary fasteners and two-part fasteners. Unitary fasteners generally include a pair of legs adapted to penetrate tissue and connected by a backspan from which they extend. In use, the unitary fasteners are formed by driving them into the depressions formed on the anvil, and subsequent to formation, the unitary fasteners have a "B" shaped configuration. Typically, the two-part fastener includes legs that are barbed and connected by a backspan which are engaged and locked into a separate retainer piece that is usually located in the anvil. In use, the two-part fastener is pressed into the tissue so that the barbs penetrate the tissue and emerge from the other side where they are then locked into the retainer piece. The retainers prevent the two-part fastener from dislodging from the tissue. The two-part fasteners are not intended to be unlocked or removable. For this reason, they are generally made of a bioabsorbable material.

During each of the aforementioned surgical procedures, the tissue is initially gripped or clamped such that individual fasteners can be ejected from the cartridge, through the slots, and forced through the clamped tissue.

A common concern in each of these procedures is hemostasis, or the rate at which bleeding of the target tissue is stopped. It is commonly known that by increasing the amount of pressure applied to a wound, the flow of blood can be limited, thereby decreasing the time necessary to achieve hemostasis. To this end, conventional surgical fastening apparatus generally apply two or more rows of fasteners about the cut-line to compress the surrounding tissue in an effort to stop any bleeding and to join the cut tissue together. Each of the fasteners will generally apply a compressive force to the tissue sufficient to effectuate hemostasis, however, if too much pressure is applied, this can result in a needless reduction in blood flow to the tissue surrounding the cut-line. Accordingly, the joining of tissue together in this manner may result in an elevated level of necrosis, a slower rate of healing, and/or a greater recovery period.

Consequently, it would be advantageous to provide a surgical fastening apparatus capable of limiting the flow of blood in the tissue immediately adjacent the cut tissue to effectuate hemostasis and wound closure, while maximizing blood flow in the surrounding tissue to facilitate healing.

Additionally, when tissue is clamped and compressed between the anvil and cartridge, some of the fluid of the tissue is squeezed out in preparation for receiving the fasteners. It would be advantageous to provide staples which could better accommodate different tissue thicknesses.

SUMMARY

The present disclosure is directed towards surgical stapling instruments configured to effectuate an improved balance between the anastomotic strength and the degree of hemostasis at the tissue interface. In particular, embodiments of the present disclosure include surgical fasteners of different sizes. Further still, the distance between an anvil member and a staple cartridge (i.e. the gap) varies along a longitudinal axis of the staple cartridge. Combining the different sizes of surgical fasteners with the varying gap between the anvil member and the staple cartridge improves the anastomotic strength and the degree of hemostasis at the tissue interface.

An end effector is disclosed herein for a surgical instrument including an operative tool having a width and a length, wherein the operative tool includes an anvil and a cartridge disposed along the length of the operative tool and defining a gap therebetween. The gap defined between the anvil and the cartridge has at least two different sizes between a first and a second end of the length of the operative tool. The gap may be substantially constant size along the width of the operative tool. The anvil and the cartridge are adapted to grasp tissue therebetween such that a pressure corresponding to the size of the gap between the anvil and the cartridge is applied to the tissue. The value of the pressure between the first end and the second end is not constant and may define a pressure gradient.

According to one aspect of the disclosure, the surgical stapling instrument includes a first structure defining an anvil member operatively associated therewith, and a second structure defining a staple cartridge operatively associated therewith. The staple cartridge has a tissue contacting surface with a stepped profile. The tissue contacting surface of the staple cartridge also includes a plurality of retention slots formed therein for retaining a surgical fastener. During operation of the surgical stapling instrument, the anvil member and the staple cartridge can be approximated relative to one another. The surgical fasteners may include a backspan and a pair of legs that have a length corresponding to the size of the gap between the anvil and the cartridge.

In one embodiment, the staple cartridge includes a first section having a first tissue contacting surface that defines a first gap between the first tissue contacting surface and the tissue contacting surface of the anvil member. In addition, the staple cartridge includes a second section and a third section having second and third tissue contacting surfaces that define second and third gaps between the second and third tissue contacting surfaces and the tissue contacting surface of the anvil member. The first gap may be different from the second gap and/or the third gap such that the tissue contacting surfaces form a stepped profile.

The cartridge may also include a plurality of receiving sections adjacently positioned along an axis of the cartridge. Each receiving section is adapted to receive a removable tissue contacting section therein. Each of the removable tissue contacting sections has a tissue contacting surface. A clinician may position the removable contacting sections within the receiving sections and position the sections adjacent to one another to adjust the size of the gap between the tissue contacting surfaces and the anvil. By adjusting the size of the gap, the pressure applied to tissue when grasped between the anvil and the cartridge may be adjusted.

The presently disclosed surgical stapling instruments, together with attendant advantages, will be more clearly illustrated below by the description of the drawings and the detailed description of the embodiments. Other objects and features of the present disclosure will become apparent from consideration of the following description taken in conjunction with the accompanying drawings.

BRIEF DESCRIPTION OF THE DRAWINGS

Embodiments of the presently disclosed surgical stapling apparatus are described herein with reference to the accompanying drawings, wherein.

DETAILED DESCRIPTION OF EMBODIMENTS

Figure 1:
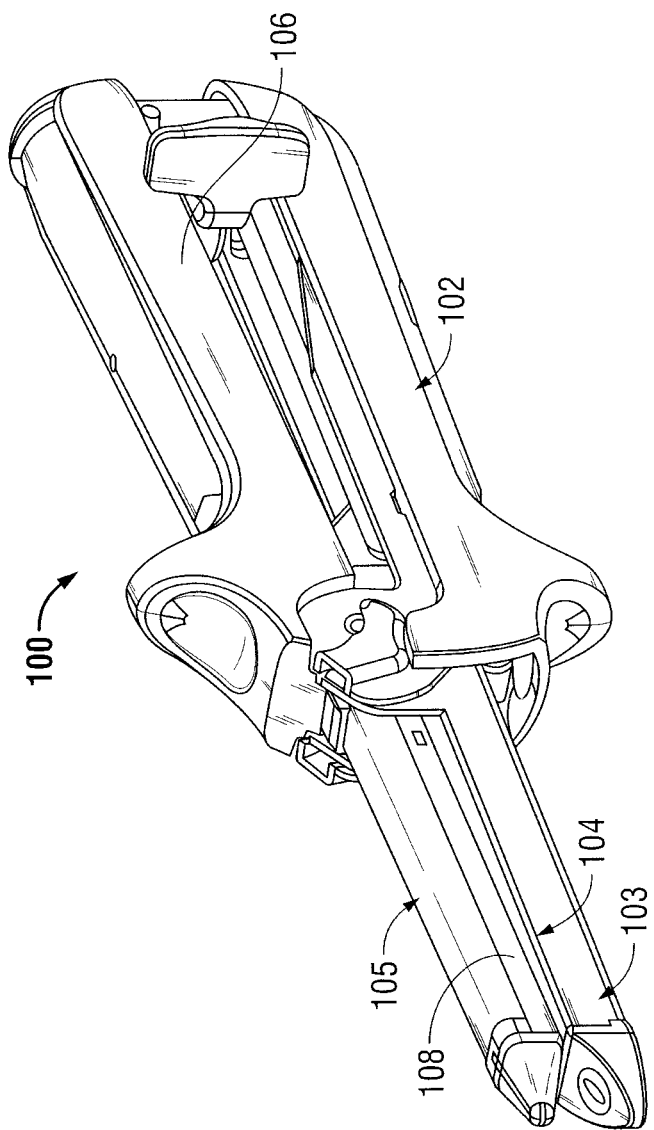
FIG. 1 is a perspective view of a surgical stapling instrument in accordance with an embodiment of the present disclosure.

Embodiments of the presently disclosed surgical stapling instruments will now be described in detail with reference to the drawing figures wherein like reference numerals identify similar or identical elements. In the drawings and in the description which follows, the term "proximal", as is traditional, will refer to the end of the surgical stapling instrument which is closest to the operator while the term "distal" will refer to the end of the device which is furthest from the operator.

Turning now to FIG. 1, a surgical stapling instrument, of the gastro-intestinal anastomosis type for performing surgical anastomotic stapling, in accordance with an embodiment of the disclosure, is generally designated as 100. Surgical stapling instrument 100 includes a first handle 102 having a jaw 103 defining a staple cartridge receiving section extending from a distal end thereof, a staple cartridge 104 receivable in jaw 103, a second handle 106 having a jaw 105 defining an anvil member receiving section extending from a distal end thereof, and an anvil member 108 operatively associated with jaw 105. First and second handles 102, 106 are configured such that staple cartridge 104 is substantially aligned with anvil member 108.

In operation, surgical stapling instrument 100 is fired similarly to and in accordance with other known surgical stapling instruments. An example of a surgical stapling apparatus and methods for its use are is disclosed in U.S. Pat. No. 6,202,914, currently assigned to Tyco Healthcare Group LP, the entire contents of which is hereby incorporated herein by reference. The cartridge 104 defines a plurality of slots and a tissue contacting surface. A plurality of surgical fasteners is disposed in the slots of the cartridge 104. Adjacent to the surgical fasteners are ejectors or pushers. By moving the first and second handles 102, 106 towards each other, an actuator mounted within the cartridge 104 translates therein to transmit a driving force to the ejectors or pushers to thereby eject the surgical fasteners from the slots and driven against an staple forming surface of the anvil member 108. Sequential firing of the surgical fasteners may continue until all the staples once housed in the cartridge 104 are ejected.

Figure 2:
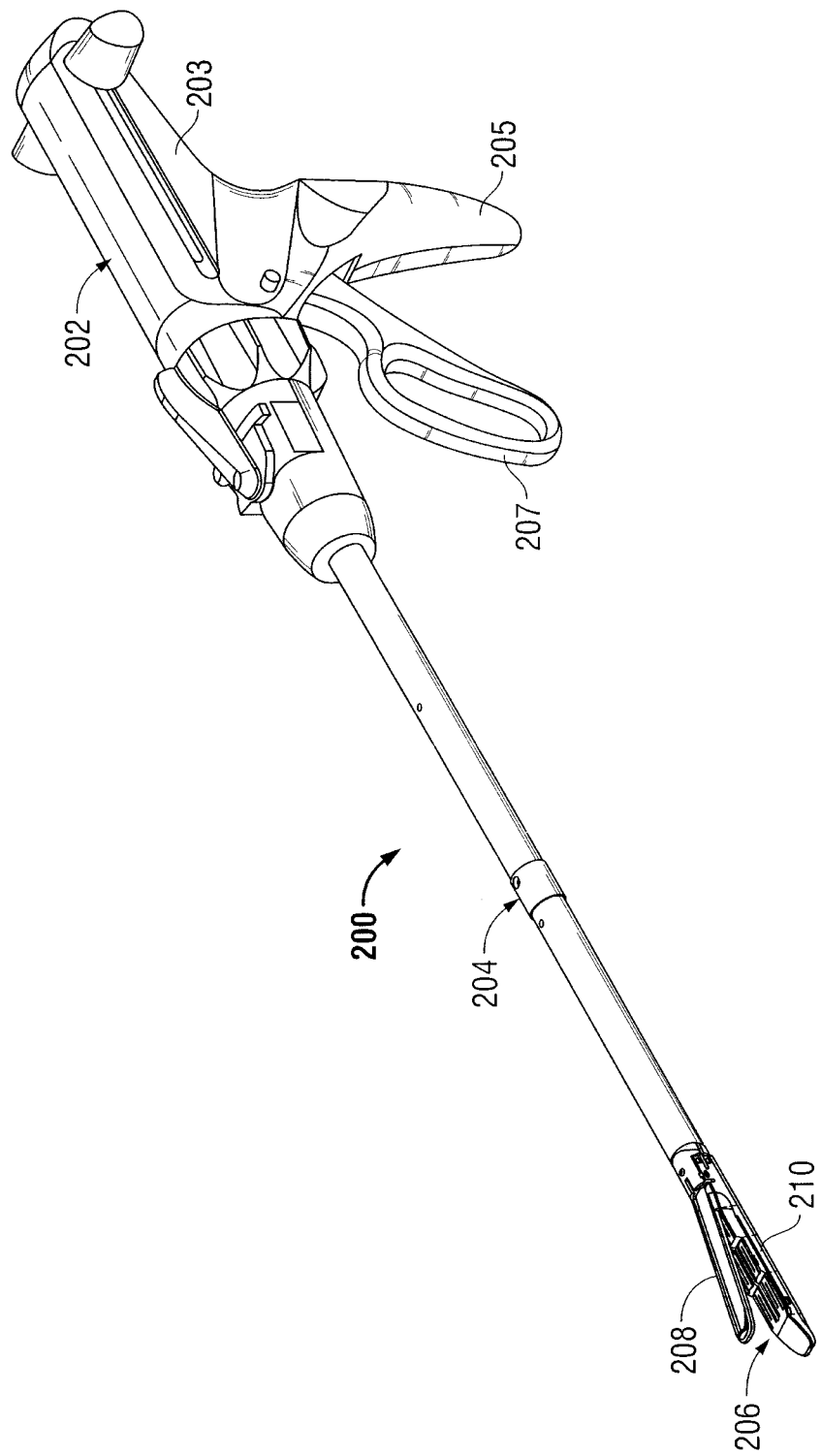
FIG. 2 is a perspective view of a surgical stapling instrument in accordance with an alternate embodiment of the present disclosure.

Turning now to FIG. 2, a surgical stapling instrument, of the laparoscopic type for performing surgical anastomotic stapling, in accordance with another embodiment of the disclosure, is generally designated as 200. Surgical stapling instrument 200 includes a handle assembly 202, an operative tool 206, and an elongated shaft 204 for interconnecting operative tool 206 to handle assembly 202. In general, operative tool 206 is designed to clamp over and then to staple and divide tissue held therein. Accordingly, as seen in FIG. 2, operative tool 206 is a pair of opposed jaws including an anvil member 208 and a staple cartridge 210 pivotally coupled to one another.

In operation, surgical stapling instrument 200 is fired similarly to and in accordance with other known surgical stapling instruments. For a detailed discussion of the approximation and firing of surgical stapling instrument 200, reference is made to commonly assigned U.S. Pat. No. 5,865,361, currently assigned to Tyco Healthcare Group LP, the entire contents of which is hereby incorporated herein by reference. The handle assembly 202 includes a housing 203, which includes stationary handle member 205. A movable handle 207 is pivotably supported within the housing 203 and is biased away from the stationary handle member 205. Movement of the movable handle 207 in the direction of the stationary handle member 205 urges the anvil member 208 towards the staple cartridge 210 such that the anvil member 208 and the staple cartridge 210 are in close cooperative alignment. Subsequently, continued movement of movable handle 207 imparts a driving force to an actuation shaft within the housing 202 causing it to advance linearly in a distal direction. The anvil member 208 and the staple cartridge 210 are moved closer relative to each other and a force is transmitted to the ejectors or pushers positioned adjacent to surgical fasteners disposed within slots of the staple cartridge 210 to thereby eject the surgical fasteners and to drive the surgical fasteners against a staple forming surface of the anvil member 208.

Figure 3:
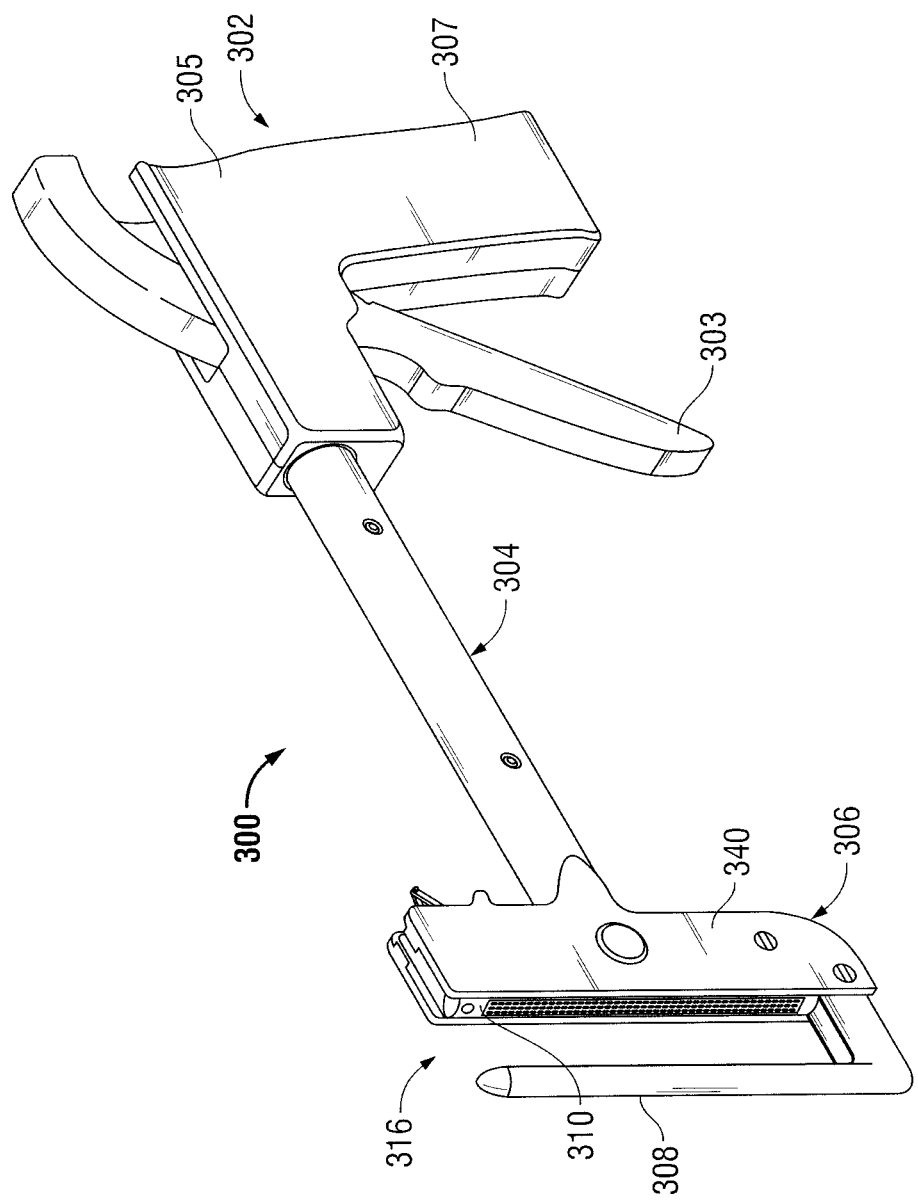
FIG. 3 is a perspective view of a surgical stapling instrument in accordance with a further embodiment of the present disclosure.

Turning now to FIG. 3, a surgical stapling instrument 300, of the transverse anastomosis type for performing surgical anastomotic stapling, in accordance with yet another embodiment of the disclosure, is generally designated as 300. Surgical stapling instrument 300 includes a handle assembly 302, a barrel 304 extending from handle assembly 302, and an arm 306 extending from the distal end of barrel 304. Surgical stapling instrument 300 further includes an anvil member 308 orthogonally affixed to a distal end of arm 306 and a staple cartridge receiver 340 operatively coupled to the distal end of barrel 304 for holding a disposable staple cartridge 310 thereon. The anvil member 308 and the staple cartridge 310 define an operative tool 316.

In operation, surgical stapling instrument 300 is fired similarly to and in accordance with other known surgical stapling instruments. For a detailed discussion of the approximation and firing of surgical stapling instrument 300, reference is made to commonly assigned U.S. Pat. No. 5,964,394, currently assigned to Tyco Healthcare Group LP, the entire contents of which is incorporated herein by reference. The handle assembly 302 includes a housing 305, which includes a stationary handle member 307. A movable handle 303 is pivotably supported within the housing 305 and is biased away from the stationary handle member 307. Movement of the movable handle member 303 in the direction of the stationary handle member 307 imparts a driving force to an actuation shaft within the housing 305 which in turn imparts a force to a pusher bar within the staple cartridge 310 to thereby eject fasteners disposed within slots of the staple cartridge 10 and to drive the surgical fasteners against a staple forming surface of the anvil member 308.

Figure 4:
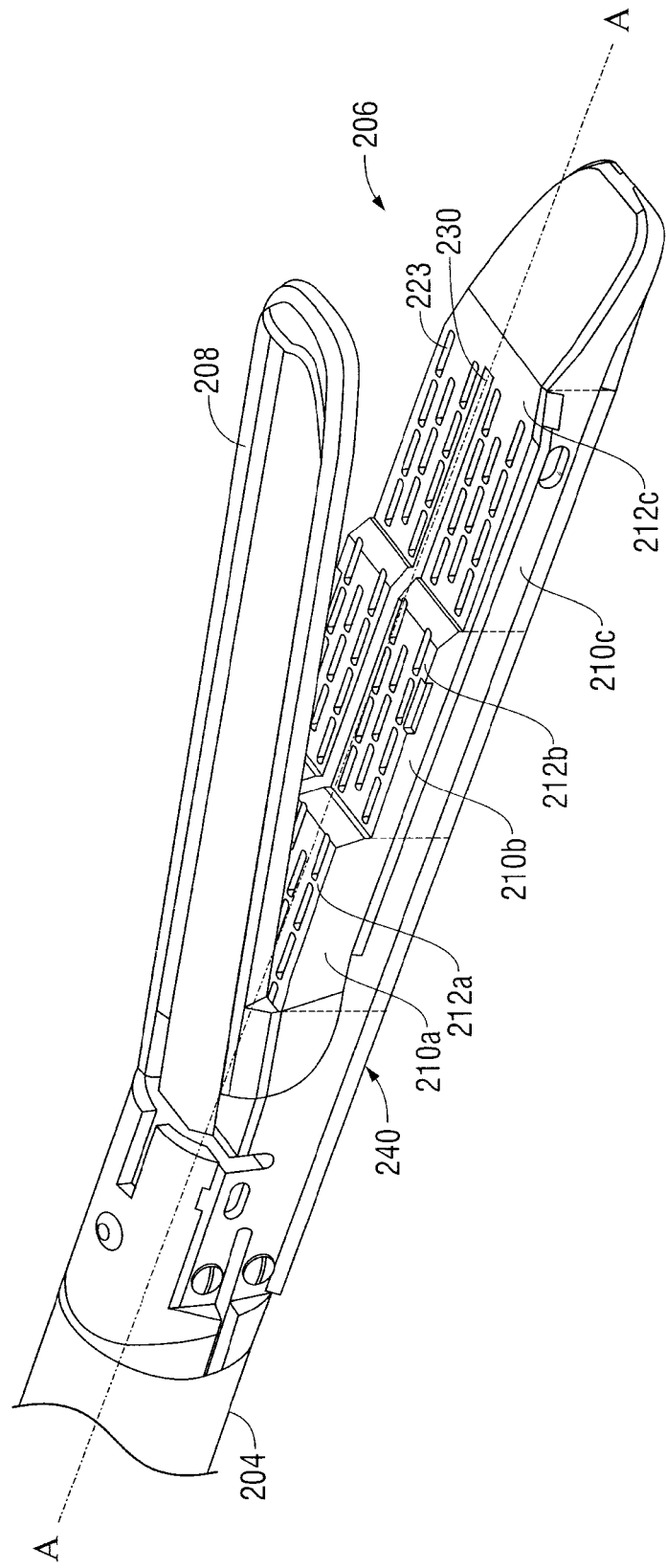
FIG. 4 is a perspective view of an end effector in accordance with an embodiment of the present disclosure.

Referring now to FIG. 4, the operative tool 206 is illustrated with the anvil member 208 in an open position. The anvil member 208 has a planar tissue contacting surface that faces towards the staple cartridge 210. Additionally, the anvil member 208 has a tissue contacting surface that includes a plurality of depressions or pockets (not shown) that are arranged for cooperating with retention slots 223 of the staple cartridge 210 for forming completed surgical fasteners. Staple cartridge 210 includes a first section 210a, a second section 210b, and a third section 210c. In the illustrated embodiment, first section 210a has a first height that defines a first gap between the anvil member 208 and first tissue contacting surface 212a. Similarly, second and third sections 210b, 210c have second and third heights, respectively, that define second and third gaps between the anvil member 208 and tissue contacting surfaces 212b, 212c respectively. As shown in FIG. 4, the size of the first gap is less than the second gap which is less than the third gap so that the size of the gap between the anvil member 208 and staple cartridge 210 increases in the distal direction. Other arrangements of gaps are envisioned. For example, the most distal portion of the staple cartridge 210 may have the smallest gap. Alternatively, two of the sections may define the same gap with respect to the anvil member 208. Further still, the operative tool 206 may include a channel 230 for accommodating a cutting member (not shown) that travels along the longitudinal axis A-A of the operative tool 206.

Although illustrated as a unitary construction, it is envisioned that each of the sections 210a, 210b, and/or 210c may be individually replaceable such that the operative tool 206 may be reconfigured and adapted for different surgical procedures. As such, each section 210a, 210b, and 210c may be individually installable in the staple cartridge 210. In this configuration, the staple cartridge 210 may be reconfigured by the practitioner just prior to use, thereby providing increased flexibility of the instrument by allowing the practitioner to rearrange the stepped configuration of the gaps according to the surgical procedure to be performed.

In further embodiments, the anvil member may have a tissue contacting surface with a height that varies along the longitudinal axis. The heights of the tissue contacting surfaces of the anvil, the cartridge, or both, vary to accommodate tissue of different thicknesses.

Although the arrangement of the staple cartridge sections are discussed with respect to the operative tool 206, the above-mentioned arrangements and configurations are readily adaptable for use with surgical stapling apparatus 100 as well.

Figure 5:
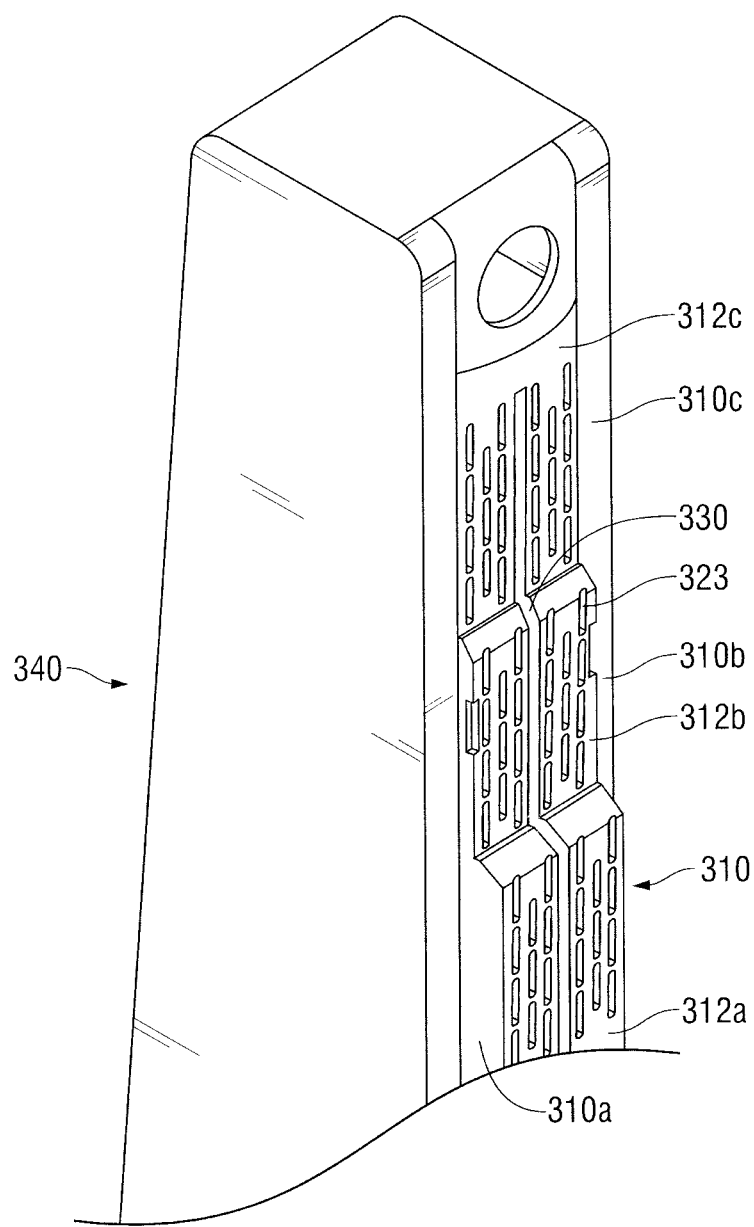
FIG. 5 is a perspective view of an end effector in accordance with an alternate embodiment of the present disclosure.

Referring now to FIG. 5, a further embodiment of the staple cartridge is disclosed and generally identified as 310. Staple cartridge 310 is disposed in a staple cartridge receiver 340 and defines a tissue contacting surface. Similar to previously discussed staple cartridge 210, staple cartridge 310 includes a first section 310a, a second section 310b, and a third section 310c. In the illustrated embodiment, first section 310a has a first height that defines a first gap between an anvil member 308 and first tissue contacting surface 312a. Similarly, second and third sections 310b, 310c have second and third heights, respectively, that define second and third gaps between the anvil member 308 and tissue contacting surfaces 312b, 312c respectively. Other arrangements of gaps are envisioned. For example, the portion of the staple cartridge 310 at one end of the staple cartridge receiver 340 may have the smallest gap. Alternatively, two of the sections may define the same gap with respect to the anvil member 308. Further still, the operative tool 316 may include a channel 330 for guiding a cutting member (not shown) along the longitudinal axis of the operative tool 306. Additionally, the anvil member 308 includes a plurality of depressions or pockets (not shown) that are arranged for cooperating with retention slots of 323 of the staple cartridge 310 for forming completed surgical fasteners.

It is contemplated that the operative tool 316 may have an anvil member with a tissue contacting surface with a height that varies along the longitudinal axis of the anvil member defining a stepped configuration similar to that of the staple cartridge 310. The stepped configuration of the tissue contacting surface of the anvil member 308 may be complementary to that of the tissue contacting surface of the staple cartridge 310 and defining a tissue compression gradient along the longitudinal axis of the operative tool 316. In particular, the stepped configuration of the tissue contacting surfaces of the anvil member 308 and the staple cartridge 310 vary in tandem. Alternatively, the tissue contacting surface of the anvil member 308 may have a stepped configuration that varies in opposition to the stepped configuration of the tissue contacting surface of the staple cartridge 310. Other combinations of gaps formed between the tissue contacting surfaces of the anvil member 308 and the staple cartridge 310 are envisioned. It is further contemplated that any of these arrangements are adaptable for use in operative tool 206.

Although illustrated as a unitary construction, it is envisioned that each of the sections 310a, 310b, and/or 310c may be individually replaceable such that the operative tool 316 may be reconfigured and adapted for different surgical procedures. As such, each section 310a, 310b, and 310c may be individually installable in the staple cartridge 310. In this configuration, the staple cartridge 310 may be reconfigured by the practitioner just prior to use, thereby providing increased flexibility of the instrument by allowing the practitioner to rearrange the stepped configuration of the gaps according to the surgical procedure to be performed.

Additionally, it is envisioned that the operative tool 206 or staple cartridge 310 may be included in a kit that also includes additional sections of varying heights that allow the practitioner to install the desired sections for the procedure to be performed. For instance, the kit may include the operative tool 206 or staple cartridge 310 and a plurality of staple cartridge sections (i.e. 210a, 210b, 210c or 310a, 310b, 310c). Thus, the practitioner may select and install the desired sections and form the staple cartridge 210 or 310 with a configuration suitable for the procedure to be performed. As envisioned, the practitioner may, by way of example only, select and arrange the sections such that the first gap is the largest, the intermediary or second gap is less than the first gap, and the third gap is the smallest. Similarly, the practitioner may select and arrange the staple cartridge sections such that the first and third gaps are identical with the second gap being different. Other combinations using individually selectable staple cartridge sections may be chosen by the practitioner.

Regardless of whether the staple cartridge sections are individually selectable or the staple cartridge is supplied as a unitary structure, the operative tool 206 or staple cartridge 310 provides a tissue compression gradient when tissue is captured between the tissue contacting surface of the anvil member 208, 308 and the surfaces of the staple cartridge 210 or 310. Tissue or layers of tissue positioned between first tissue contacting surface 212a, 312a and the anvil member 208, 308 is compressed to a first value when the anvil member 208, 308 is approximated with the staple cartridge 210, 310. Similarly, tissue or layers of tissue positioned between second and third tissue contacting surfaces 212b, 312b and 212c, 312c and the anvil member 208, 308 are compressed to respective second and third values when the anvil member 208, 308 is approximated with the staple cartridge 210, 310. The first value is greater than the second value which is greater than the third value, thereby providing a tissue compression gradient that decreases from the proximal portion of the operative tool 206 towards the distal portion of the operative tool 206 or from a first region towards a second region of operative tool 316. As discussed hereinabove, the arrangement of gaps may be altered in view of the surgical procedure to be performed, thereby allowing the practitioner to vary the tissue compression gradient as needed.

In addition, the operative tool 206, 316 is suitable for procedures involving organs or sections of the patient's body that have thin sections of tissue adjacent thicker sections of tissue, where the variation in the tissue thickness is along the longitudinal axis of the operative tool 206, 316. The operative tool 206, 316 is arranged to accommodate differences in the thickness of the tissue. For example, in a wedge resection of lung tissue using operative tool 206, the tissue at the distal end of staple cartridge 210 is thicker than tissue at the proximal end of the staple cartridge 210.

Figure 6:
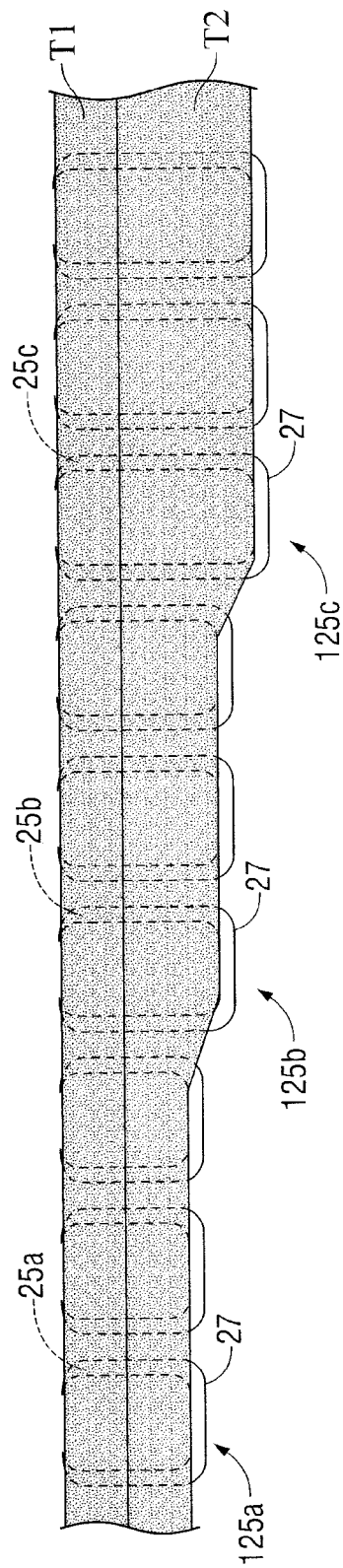
FIG. 6 is a side cross-sectional view of the resulting tissue interface following the firing of the surgical stapling instrument of FIGS. 1-3.

Turning now to FIG. 6, a cross-section of the resulting tissue interface, following the firing of staple cartridge 210, 310, is shown. As seen in FIG. 6, the tissue interface has a stepped profile. An example of a staple cartridge having a tapered or stepped profile can be seen in U.S. Pat. No. 7,398, 908, the contents of which are hereby incorporated by reference. The distance between an anvil member and a staple cartridge, i.e., a gap, may vary from a centerline of the staple cartridge to an outer edge of the staple cartridge. Surgical fasteners including a pair of legs and a backspan have a leg length that corresponds to the gap.

Each retention slot 223, 323 is configured and dimensioned to retain a staple or surgical fastener 125 (FIG. 6) therein. Each surgical fastener 125 includes a backspan 27 and a pair of depending legs 25. Legs 25a of surgical fasteners 125a have a first leg length, legs 25b of surgical fasteners 125b have a second leg length, and legs 25c of surgical fasteners 125c have a third leg length. In one embodiment, legs 25c of surgical fasteners 125c have a leg length of about 2.3 mm, legs 25b of surgical fasteners 125b have a leg length of about 3.5 mm, and legs 25a of surgical fasteners 125a have a leg length of about 4.1 mm.

Using this configuration, surgical fasteners 125a having the shortest leg lengths are deployed in first section 210a, 310a (i.e. having the smallest gap), while surgical fasteners 125b, 125c are disposed respectively in sections 210b, 310b and 210c, 310c having larger gaps. In the illustrated embodiment, layers of tissue T1, T2 are joined together using one of the presently disclosed surgical stapling instruments 100, 200, 300. The region of the operative tool 206, 316 having the smallest gap employs surgical fasteners 125a and compressing tissue layers T1, T2 by a first predetermined amount for a first tissue pressure. Similarly, the region of the operative tool 206, 316 having a larger gap employs surgical fasteners 125b, thereby compressing tissue layers T1, T2 by a second predetermined amount for a second tissue pressure. Finally, the region of the operative tool 206, 316 having the greatest gap employs surgical fasteners 125c, thereby compressing tissue layers T1, T2 by a third predetermined amount for a third tissue pressure. The thickness of the tissue in relation to the plurality of gaps contributes to the values of the plurality of tissue pressures. As previously disclosed, the arrangement of the gaps may be altered either during the manufacturing process or by utilizing discrete sections of the staple cartridge for the physician to field modify the operative tool.

By providing tissue contacting surfaces 212a, 212b, 21c or 312a, 312b, 312c in a stepped configuration, the anastomotic strength and the degree of hemostasis at the tissue interface improves when layers of body tissue are clamped between anvil member 208,308 and staple cartridge 210, 310. In particular, this arrangement provides gradual tissue loading or compression due to the varying gap defined between anvil member 208,308 and staple cartridge 210,310 when they are in the approximated position (i.e. they are substantially parallel to one another), thereby minimizing tissue trauma while maintaining a relatively high degree of hemostasis and anastomotic strength. Embodiments of a surgical stapling instrument can be used to provide a variable pressure gradient (i.e. load profile) to the layers of tissue that are joined together with the surgical fasteners. Therefore, the layers of tissue that are located in the region with the smallest gap between the anvil member and the staple cartridge are subjected to higher compressive forces (i.e. loads), as compared to layers of tissue that are in regions of the surgical stapling instrument having larger gaps between the anvil member and the staple cartridge. Since the layers of tissue in the first gap can be compressed more, a smaller sized (i.e. shorter leg lengths, shorter backspans, or both) surgical staple or fastener can be used to mechanically suture (i.e. fasten) the layers of tissue. Further still, providing a gradual compression gradient to the layers of tissue to be joined, may result in a higher degree of hemostasis and/or better staple formation.

In contexts where the thickness of the tissue to be stapled or joined varies, embodiments of the surgical stapling instrument according to the present disclosure can be used to accommodate different thicknesses by deploying larger sized staples (i.e. longer leg lengths, longer backspans, or both) in thicker tissue and smaller sized staples (i.e. shorter leg lengths, shorter backspans, or both) in thinner tissue, for better staple formation and improved hemostasis.

It will be understood that various modifications may be made to the embodiments of the presently disclosed surgical stapling instruments. Therefore, the above description should not be construed as limiting, but merely as exemplifications of embodiments. Those skilled in the art will envision other modifications within the scope and spirit of the present disclosure.

What is claimed is:

1. A surgical instrument, comprising:
an anvil including an anvil tissue contacting surface; and
a cartridge adapted to connect to a jaw member of the surgical instrument including a first section having a first cartridge tissue contacting surface and a second section having a second cartridge tissue contacting surface, each of the first and second cartridge tissue contacting surfaces including retention slots for the retention of surgical fasteners therein, the first section and the second section being removably couplable to the cartridge,
wherein the anvil and the cartridge define a first gap between the first cartridge tissue contacting surface of the cartridge and the tissue contacting surface of the anvil and a second gap between the second cartridge tissue contacting surface of the cartridge and the tissue contacting surface of the anvil, the first gap defining a first distance between the first cartridge tissue contacting surface of the cartridge and the tissue contacting surface of the anvil, the second gap defining a second distance between the second cartridge tissue contacting surface of the cartridge and the tissue contacting surface of the anvil, the first distance being different than the second distance, the first gap and the second gap being spaced apart along a longitudinal axis of the end effector.

2. The surgical instrument of claim 1, wherein approximation of the anvil and the cartridge applies pressure to tissue positioned therebetween.

3. The surgical instrument of claim 2, wherein approximation of the anvil and the cartridge and the clamping of tissue therebetween produces a first value of pressure applied at the first gap, and a second value of pressure applied at the second gap.

4. The surgical instrument of claim 1, wherein the cartridge includes a plurality of surgical fasteners disposed therein.

5. The surgical instrument of claim 4, wherein each of the first section and the second section have a plurality of surgical fasteners disposed therein.

6. The surgical instrument of claim 5, wherein each of the surgical fasteners include a backspan and a pair of legs.

7. The surgical instrument of claim 6, wherein the legs of the fasteners of the first section have a different length than the legs of the fasteners of the second section.

8. The surgical instrument of claim 1, wherein each of the first section and the second section are removable and selectively positionable to adjust the size of a gap between each of the first section and the second section, and the tissue contacting surface of the anvil.

9. The surgical instrument of claim 1, wherein the first section is disposed distally of the second section, the first section defining a larger gap with the tissue contacting surface of the anvil than a gap defined by the second section and the tissue contacting surface of the anvil.

* * * * *